United States Patent [19]
Garst et al.

[11] Patent Number: 6,093,734
[45] Date of Patent: Jul. 25, 2000

[54] PRODRUGS OF PROTON PUMP INHIBITORS

[75] Inventors: Michael E. Garst, Newport Beach; George Sachs, Encino; Jai Moo Shin, Northridge, all of Calif.

[73] Assignee: Partnership of Michael E. Garst, George Sachs, and Jai Moo Shin, Newport Beach, Calif.

[21] Appl. No.: 09/131,481

[22] Filed: Aug. 10, 1998

[51] Int. Cl.$^7$ .................. A61K 31/4439; A61K 31/445; C07D 401/12; C07D 401/14; C07D 413/12

[52] U.S. Cl. .......... 514/338; 514/318; 514/235.2; 544/124; 546/273.7; 546/194

[58] Field of Search ............ 546/273.7; 514/338, 514/318, 235.2; 544/124

[56] References Cited

U.S. PATENT DOCUMENTS

| | | | |
|---|---|---|---|
| 4,045,563 | 8/1977 | Berntsson et al. | 514/338 |
| 4,255,431 | 3/1981 | Junggren et al. | 514/338 |
| 4,628,098 | 12/1986 | Nohara et al. | 546/271 |
| 4,686,230 | 8/1987 | Rainer et al. | 514/338 |
| 4,758,579 | 7/1988 | Kohl et al. | 514/338 |
| 4,965,269 | 10/1990 | Brändström et al. | 514/253 |
| 5,021,433 | 6/1991 | Alminger et al. | 514/338 |
| 5,045,552 | 9/1991 | Souda et al. | 514/338 |
| 5,430,042 | 7/1995 | Lindberg et al. | 514/338 |
| 5,708,017 | 1/1998 | Dave et al. | 514/393 |

FOREIGN PATENT DOCUMENTS

| | | |
|---|---|---|
| 00452200 | 2/1982 | European Pat. Off. . |
| 2134523 | 8/1884 | United Kingdom . |
| WO97/48380 | 12/1997 | WIPO . |

OTHER PUBLICATIONS

B.G. Katzung MD,PhD Basic & Clinical Pharmacology, sixth Edition, p. 952, 1995.

Design of prodrugs: Bioreversible derivatives for various functional groups and chemical entities, *Design of Prodrugs* (Bundgaard, H., ed.) 1985 Elsevier Science Publishers B.V. (Biomedical Division), Chapter 1, H. Bundgaard et al.

Formation of Prodrugs of Amines, Amides, Ureides, and Imides, by H. Bundgaard, *Methods in Enzimology*, vol. 112, pp. 347–359. (1998).

International Journal of Pharmaceuticals, vol. 22, 1984, pp. 45–56 (Elsevier, H. Bundgaard et al.

International Journal of Pharmaceuticals, vol. 29, 1986, pp. 19–28 (Elsevier), H. Bundgaard et al.

Journal of Medicinal Chemistry, vol. 32, No. 12, Dec. 1989, pp. 2503–2507, H. Bundgaard et al.

Chemical Abstracts, vol. 93, 1980, abstract No. 137935y, Bundgaard et al.

Chemical Abstracts, vol. 95, 1981, abstract No. 138493f, Bundgaard et al.

Chemical Abstracts, vol. 95, 1981, abstract No. 138592n, Bundgaard et al.

Chemical Abstracts, vol. 110, 1989, abstract No. 57664, Alminger et al.

Chemical Abstracts, vol. 115, 1991, abstract No. 64029s, Buur et al.

Chemical Abstracts, vol. 115, 1991, abstract No. 189582y, Hansen et al.

Chemical Abstracts, vol. 117, 1992, abstract No. 14347q, Bundgaard et al.

Chemical Abstracts, vol. 117, 1992, abstract No. 55790x, Jensen et al.

Chemical Abstracts, vol. 123, 1995, abstract No. 17593b, Thomsen et al.

*Primary Examiner*—Alan L. Rotman
*Attorney, Agent, or Firm*—Klein & Szekeres, LLP

[57] ABSTRACT

Prodrugs of the pyridyl methyl sulfinyl benzimidazole type proton pump inhibitor drugs have a hydrolyzable sulfinyl or arylsulfonyl group attached to the benzimidazole nitrogen, or include a group that forms a Mannich base with the benzimidazole nitrogen. The prodrugs of the invention hydrolyze under physiological conditions to provide the proton pump inhibitors with a half life measurable in hours, and are capable of providing sustained plasma concentrations of the proton pump inhibitor drugs for longer time than presently used drugs. The generation of the proton pump inhibitor drugs from the prodrugs of the invention under physiological conditions allows for more effective treatment of several diseases and conditions caused by gastric acid secretion.

10 Claims, No Drawings

PRODRUGS OF PROTON PUMP INHIBITORS

BACKGROUND OF THE INVENTION

1. Field of the Invention

The present invention is directed to prodrugs of proton pump inhibitors which are usefull as anti-ulcer agents. More particularly, the present invention is directed to prodrugs that slowly hydrolyze to provide benzimidazole-type proton pump inhibitors which inhibit exogenously or endogenously gastric acid secretion and thus can be used in the prevention and treatment of gastrointestinal inflammatory diseases in mammals, including humans.

2. Brief Description of the Prior Art

Benzimidazole derivatives intended for inhibiting gastric acid secretion are disclosed in the U.S. Pat. Nos. 4,045,563; 4,255,431; 4,628,098; 4,686,230; 4,758,579; 4,965,269; 5,021,433; 5,430,042 and 5,708,017. Generally speaking, the benzimidazole-type inhibitors of gastric acid secretion work by undergoing a rearrangement to form a thiophilic species which then covalently binds to gastric H,K-ATPase, the enzyme involved in the final step of proton production in the parietal cells, and thereby inhibits the enzyme. Compounds which inhibit the gastric H,K-ATPase enzyme are generally known in the field as "proton pump inhibitors" (PPI).

Some of the benzimidazole compounds capable of inhibiting the gastric H,K-ATPase enzyme have found substantial use as drugs in human medicine and are known under such names as LANSOPRAZOLE (U.S. Pat. No. 4,628,098), OMEPRAZOLE (U.S. Pat. Nos. 4,255,431 and 5,693,818), PANTOPRAZOLE (U.S. Pat. No. 4,758,579), and RABEPRAZOLE (U.S. Pat. No. 5,045,552).

The diseases treated by proton pump inhibitors and specifically by the four above-mentioned drugs include peptic ulcer, heart burn, reflux esophagitis errosive esophagitis, non-ulcer dispepsia, infection by *Helicobacter pylori,* alrynitis and asthma among others.

Whereas the proton pump inhibitor type drugs represent substantial advance in the field of human and veterinary medicine, they are not totally without shortcomings or disadvantages. The shortcomings of the presently used proton pump inhibitor (PPI) type drugs can be best explained by a more detailed description of the mode of their action, the diseases or condition against which they are employed and the circumstances of their application. Thus, acid related diseases include but are not limited to errosive esophagitis, esophageal reflux, gastric and duodenal ulcer, non-ulcer dyspepsia and infection by *Helicobacter pylori.* Current therapy of all but the infection by *H. pylori* bacteria involves treatment with drugs designed to suppress acid secretion, one type of which are the above-mentioned proton pump inhibitors.

The presently used proton pump inhibitors are pyridyl methyl sulfinyl benzimidazoles (or compounds of closely related structure) with a $pK_a$ of 4.0 to 5.0. Their mechanism of action requires accumulation in the acidic space of the parietal cell (secretory canaliculus, pH ca. 1.0) and subsequently hydrogen ion catalyzed conversion to the reactive thiophilic species that is capable of inhibiting the gastric ATPase, enzyme resulting in effective inhibition of gastric secretion. Because of this mechanism the presently used PPI type drugs require specialized gastro protection to remain active for duodenal absorption. For this reason, and due to sensitivity to degradation in the acid milieu of the stomach, oral formulations of the PPI drugs are usually enteric coated. The need for enteric coating is a shortcoming because enteric coating is expensive and moisture sensitive.

Because of the requirement for accumulation in the acid space of the parietal cell, acid secretion is necessary for the efficacy of the PPI type drugs. It was found that the plasma half life of these drugs is between 60 to 90 minutes. All acid pumps are not active at any one time, rather only about 75% are active on the average during the time the drug is present in the blood following oral administration. It was also found in medical experience that on a currently used once-a-day oral administration therapy the maximal inhibition of stimulated acid output is approximately 66%. This is due to a combination of the short plasma half life of the drug, to the limited number of acid pumps active during presentation of the drug and to the turn-over of acid pumps. In present practice it is not possible to control night time acid secretion by evening therapy of oral administration because the drug is dissipated from the plasma by the time acid secretion is established after midnight.

The ideal target for healing in acid related diseases and for treatment of *H. pylori* infection (in conjunction with antibiotics), as well as for relief of symptoms of non-ulcer dyspepsia would be full inhibition of acid secretion. With the currently used PPI type drugs this is achieved only by intravenous infusion; in case of the drug OMEPRAZOLE this requires intravenous infusion of 8 mg per hour. Clearly, there is a need in the art for a drug or drugs acting through the mechanism of PPI-type drugs which can attain or approach full inhibition of acid secretion through oral therapy.

Because of the less than full inhibition of acid secretion and less than 24 hour inhibition through oral administration that is attained by the current dosage forms of currently used PPI-type drugs, therapy for healing of gastric and duodenal ulcerations is 4 to 8 weeks. This is in spite of the fact that the generation time of surface cells of the esophagus, stomach and duodenum is approximately 72 hours. Undoubtedly the presently observed prolonged healing times with these drugs is due to inadequate acid suppression and acid related damage. The foregoing underscores the need in the art for a drug or drugs acting through the mechanism of PPI-type drugs which can attain or approach full inhibition of acid secretion through oral therapy.

As further pertinent background to the present invention, applicants note the concept of prodrugs which is well known in the art. Generally speaking, prodrugs are derivatives of per se drugs, which after administration undergo conversion to the physiologically active species. The conversion may be spontaneous, such as hydrolysis in the physiological environment, or may be enzyme catalyzed. From among the voluminous scientific literature devoted to prodrugs in general, the foregoing examples are cited: *Design of Prodrugs* (Bundgaard H. ed.) 1985 Elsevier Science Publishers B. V. (Biomedical Division), Chapter 1; Design of Prodrugs: Bioreversible derivatives for various functional groups and chemical entities (Hans Bundgaard); Bundgaard et al. *Int. J. of Pharmaceutics* 22 (1984) 45–56 (Elsevier); Bundgaard et al. *Int. J. of Pharmaceutics* 29 (1986) 19–28 (Elsevier); Bundgaard et al. *J. Med. Chem.* 32 (1989) 2503–2507 *Chem. Abstracts* 93, 137935y (Bundgaard et al.); *Chem. Abstracts* 95, 138493f (Bundgaard et al.); *Chem. Abstracts* 95, 138592n (Bundgaard et al.); *Chem. Abstracts* 110, 57664p (Alminger et al.); *Chem. Abstracts* 115, 64029s (Buur et al.); *Chem. Abstracts* 115, 189582y (Hansen et al.); *Chem.*

Abstracts 117, 14347q (Bundgaard et al.); *Chem. Abstracts* 117, 55790x (Jensen et al.); and *Chem. Abstracts* 123, 17593b (Thomsen et al.).

As far as the present inventors are aware, there are no prodrugs of the proton pump inhibitors presently in use. However, several United States patents describe compounds which can act as prodrugs of certain proton pump inhibitors. Specifically, U.S. Pat. No. 4,686,230 (Rainer et al.) describes derivatives of pyridyl methyl sulfinyl benzimidazoles which include a group designated "$R_5$" on one of the benzimidazole nitrogens. The "$R_5$" group is expected to cleave under physiological condition, or under the influence of an enzyme to provide the corresponding compound with a free N-H bond (see column 3 of U.S. Pat. No. 4,686,230). U.S. Pat. Nos. 5,021,433 (Alminger et al.), 4,045,563 (Bemtsson et al.), 4,965,269 and (Brändström et al.) also describe pyridyl methyl sulfinyl benzimidazoles where one of the nitrogens of the benzimidazole moiety bears a substituent that cleaves under physiological or enzymatic conditions.

The present invention represents further advance in the art in that it provides prodrugs of improved structure of the proton pump inhibitor type drugs and provides proof of the suitability of the prodrugs of the invention for use as prodrug of proton pump inhibitors, with improved efficacy in therapy of acid related diseases due to prolongation of the presence of the proton pump inhibitors in the body.

SUMMARY OF THE INVENTION

The present invention relates to compounds of Formula 1

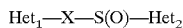

wherein $Het_1$ is

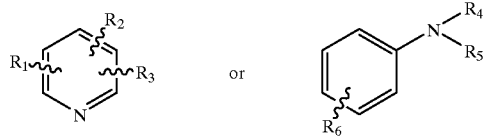

X is

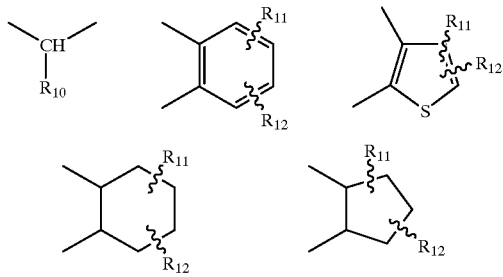

and
$Het_2$ is

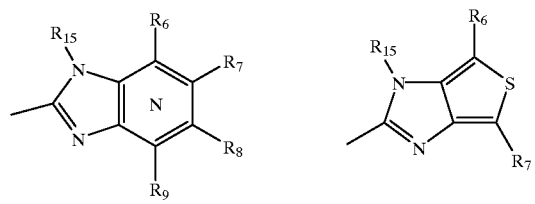

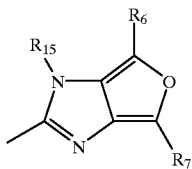

where N in the benzimidazole moiety means that one of the ring carbons may be exchanged for an unsubstituted N atom;

$R_1$, $R_2$ and $R_3$ are independently selected from hydrogen, alkyl of 1 to 10 carbons, fluoro substituted alkyl of 1 to 10 carbons, alkoxy of 1 to 10 carbons, fluoro substituted alkoxy of 1 to 10 carbons, alkylthio of 1 to 10 carbons, fluoro substituted alkylthio of 1 to 10 carbons, alkoxyalkoxy of 2 to 10 carbons, amino, alkylamino and dialkylamino each of the alkyl groups in said alkylamino and dialkyl amino groups having 1 to 10 carbons, halogen, phenyl, alkyl substituted phenyl, alkoxy substituted phenyl, phenylalkoxy, each of the alkyl groups in said alkyl substituted phenyl, alkoxy substituted phenyl and phenylalkoxy having 1 to 10 carbons, piperidino, morpholino or two of the $R_1$, $R_2$ and $R_3$ groups jointly forming a 5 or 6 membered ring having 0 or 1 heteroatom selected from N, S and O;

$R_4$ and $R_5$ are independently selected from hydrogen, alkyl of 1 to 10 carbons, fluoro substituted alkyl of 1 to 10 carbons, phenylalkyl, naphthylalkyl and heteroarylalkyl, alkyl in said phenylalkyl, naphthylalkyl and heteroarylalkyl groups having 1 to 10 carbons;

$R_6$, is hydrogen, halogen, alkyl of 1 to 10 carbons, fluoro substituted alkyl of 1 to 10 carbons, alkoxy having 1 to 10 carbons or fluoro substituted alkoxy having 1 to 10 carbons;

$R_6$ through $R_9$ are independently selected from hydrogen, alkyl of 1 to 10 carbons, halogen substituted alkyl of 1 to 10 carbons, alkoxy of 1 to 10 carbons, halogen substituted alkoxy of 1 to 10 carbons, alkylcarbonyl, alkoxycarbonyl the alkyl group in said alkylcarbonyl and alkoxycarbonyl having 1 to 10 carbons, oxazolyl, imidazolyl, thiazolyl, pyrazolyl, or any two adjacent ones of the $R_6$ through $R_9$ groups may form a ring that may optionally include a heteroatom selected from N, O and S and said ring may be further substituted;

$R_{10}$ is hydrogen, alkyl of 1 to 10 carbons, or $R_{10}$ may form an alkylene chain together with $R_3$, $R_{11}$ and $R_{12}$ are independently selected from hydrogen, halogen, alkyl of 1 to 10 carbons and halogen substituted alkyl of 1 to 10 carbons;

$R_{15}$ is

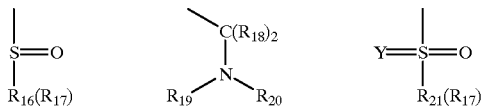

where
$R_{16}$ is alkyl of 1 to 10 carbons, morpholino, piperidino, phenyl, naphthyl or heteroaryl having 1 to 3 heteroatoms selected from N, O or S, said morpholino, piperidino phenyl, naphthyl or heteroaryl groups being unsubstituted, or substituted with 1 to 5 $R_{17}$ groups;

$R_{17}$ is alkyl of 1 to 10 carbons, halogen substituted alkyl of 1 to 10 carbons, alkoxy having 1 to 10 carbons, halogen substituted alkoxy of 1 to 10 carbons, alkylthio having 1 to 10 carbons, halogen substituted alkylthio of 1 to 10 carbons, alkoxy carbonyl having 1 to 10 carbons, halogen substituted alkoxy carbonyl having 1 to 10 carbons, F, Cl, Br, I, $NO_2$, CN, OCOalkyl, $NH_2$, alkylamino and dialkylamino where in said OCOalkyl,, alkylamino and dialkylamino groups each of said alkyl group has 1 to 10 carbons;

$R_{18}$ is independently selected from H, alkyl of 1 to 10 carbons and phenyl;

$R_{19}$ and $R_{20}$ are independently selected from H, alkyl of 1 to 10 carbons, halogen substituted alkyl of 1 to 10 carbons, or $R_{19}$ and $R_{20}$ together with the N atom may form a 4 to 10 membered ring that may include one more heteroatom selected from N, O or S, said N heteroatom being unsubstituted or substituted with an alkyl group of 1 to 10 carbons, or with an aryl or heteroaryl group, and $R_{21}$ is phenyl, naphthyl or heteroaryl having 1 to 3 heteroatoms independently selected from N, O and S, said phenyl, naphthyl or heteroaryl groups being unsubstituted or substituted with 1 to 5 $R_{17}$ groups, Y is O or $=NR_{16}$, or to a pharmaceutically acceptable salt of said compounds.

The compounds of the invention are suffoxides and have an asymmetric center in the sulfur atom. Both the pure enatiomers, racemic mixtures and unequal mixtures of the two are within the scope of the present invention. Some of the compounds of the invention may have one or more asymmetric carbon atoms (for example in a branch-chained alkyl group) and some other compounds may have a second sulfoxide providing still another asymmetric center in the sulfur atom. All optical isomers, racemates, diastereomers and their mixtures are within the scope of the invention.

The compounds of the invention act as prodrugs of proton pump inhibitor type drugs which are useful for inhibiting gastric acid secretion. The compounds of the invention have excellent stability in tablet or capsule form, are acid stable, have excellent bioavailability and plasma half life extending up to 5–6 hours which is significantly longer than the plasma half life of the presently used proton pump inhibitors.

DETAILED DESCRIPTION OF THE INVENTION

The chemical structure of the compounds of the invention is shown and described in broad terms in the Summary of the Invention in connection with Formula 1. As it can be seen in the formula, the compounds of the invention are pyridyl methyl sulfinyl benzimidazoles, or compounds of closely related structure, wherein one of the benzimidazole nitrogens is substituted with a group (designated $R_{15}$ in Formula 1) that gradually cleaves under physiological conditions and thereby provides the pyridyl methyl sulfinyl benzimidazole compound (or compound of closely related structure) which has a free N-H function in the benzimidazole (or related) moiety. The compound thus obtained by cleavage of the $R_{15}$ group then undergoes the acid catalyzed rearrangement and provides the thiophilic species which inhibits the H,K-ATPase enzyme involved in gastric acid production. Thus, the novel compounds of the present invention bearing the $R_{15}$ group are prodrugs of the proton pump inhibitor compounds which could also be depicted by Formula 1, where, however the $R_{15}$ group would be designated hydrogen.

Generally speaking, among the prodrugs compounds of the present invention those are preferred wherein the structure of the pyridyl methyl sulfinyl benzimidazole or structurally related moiety is also preferred in the prior art. In other words, preferably prodrugs are provided in accordance with the present invention for those proton pump inhibitor drugs which are themselves preferred.

Referring now to the specific designation of symbols in connection with Formula 1, compounds are preferred in accordance with the present invention wherein the moiety designated $Het_1$ is pyridyl substituted with alkyl, O-alkyl and/or O-fluoroalkyl groups. Most preferred substituents for the pyridine moiety, designated $R_1$, $R_2$ and $R_3$ in Formula 1, are $CH_3O—$, $CH_3—$, $CF_3CH_2O—$ and $CH_3O(CH_2)_3O—$.

The moiety designated X in Formula 1 is preferably a methylene ($—CH_2—$) group, or a $—CHR_{10}$ group and the methylene or $—CHR_{10}$ group is preferably attached in a position to the nitrogen in the pyridine moiety. Compounds where the X is ortho phenylene or substituted ortho phenylene are also preferred; in the most preferred compounds X is methylene.

Referring now to the group designated $Het_2$ in Formula 1, this moiety is preferably a substituted benzimidazole. The $R_6$ through $R_9$ groups preferably are selected from hydrogen and fluoro-substituted alkoxy groups, with hydrogen, $CF_2HO—$ and $CH_3O—$ being even more preferred.

Referring now to the group designated $R_{15}$ in connection with Formula 1 it will be apparent to those skilled in the art that this group represents the principal novel structural feature of the present invention. Among the $R_{15}$ groups shown in connection with Formula 1 the arylsulfonyl groups (designated $R_{21}(R_{17})SOY—$ where Y is O) are preferred. In the arylsulfonyl groups the aryl portion ($R_{21}$) is preferably phenyl, substituted or unsubstituted with the $R_{17}$ group. When the phenyl group ($R_{21}$) is substituted, then the substituent ($R_{17}$) is preferably selected from Cl, Br, F, lower alkyl, lower alkoxy, trifluoromethyl, trifluoromethoxy, di-(lower alkyl)amino, and lower alkoxycarbonyl. Even more preferably the phenyl group is unsubstituted ($R_{17}$ is H) or the substituent of the phenyl ($R_{21}$) group is selected from Cl, Br, F, methyl, methoxy, trifluoromethyl, trifluoromethoxy, dimethylamino and ethoxycarbonyl groups. Preferably there is only one $R_{17}$ substituent (other than hydrogen) in the phenyl ($R_{21}$) moiety, and preferably the $R_{17}$ substituent is in a position para (1,4) or meta (1,3) to the sulfonyl ($SO_2$) group.

In other embodiments of the compounds of the invention the physiologically labile substituent $R_{15}$ is a sulfinyl group, designated $R_{16}(R_{17})SO—$ in connection with Formula 1. Preferred groups for the $R_{16}(R_{17})$ combination are the same as for the $R_{21}(R_{17})$ combination, still more preferred are phenyl, 4-methylphenyl, 4-methoxyphenyl and 4-trifluoromethylphenyl. In this specification lower alkyl or lower alkoxy has 1 to 6 carbons.

In still other embodiments of the compounds of the invention the physiologically labile substituent $R_{15}$ forms a Mannich base, designated $R_{19}R_{20}N—C(R_{18})_2—$ in connection with Formula 1. In these Mannich base type compounds $R_{18}$ is preferably H or lower alkyl, most preferably H or methyl. The $R_{19}R_{20}N$ groups preferably are di-(lower alkyl) amino, N-succinimidyl, N-morpholinyl, N-piperidinyl, N-(N-4-methyl)hexahydropyrazinyl, N,N-phenyl,methylamino, and N-tetrahydropyrrolyl, as depicted below and designated respectively by formulas 2 through 8:

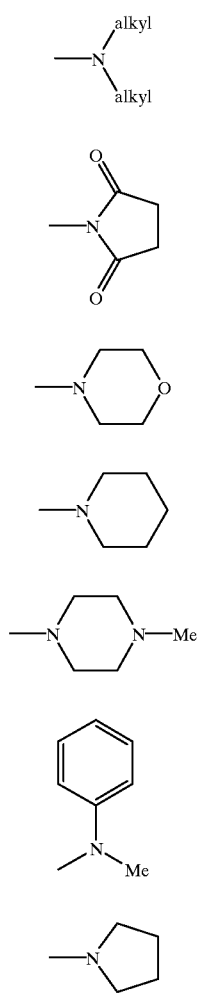

Formula 2

Formula 3

Formula 4

Formula 5

Formula 6

Formula 7

Formula 8

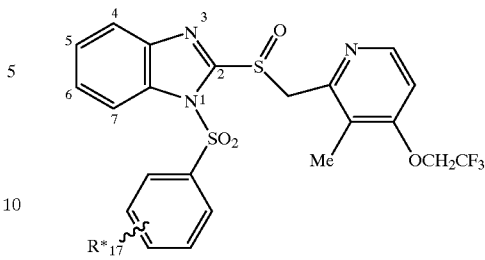

Formula 9

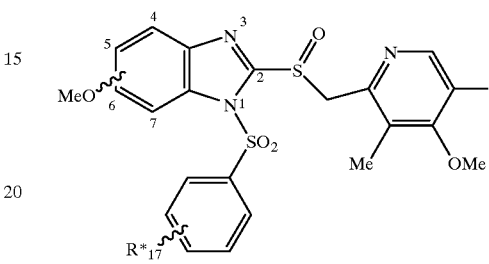

Formula 10

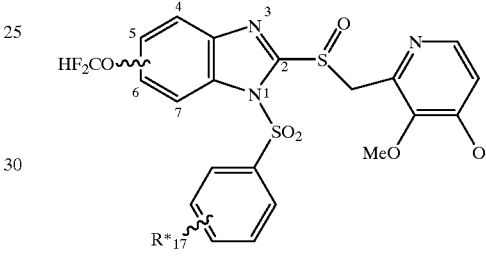

Formula 11

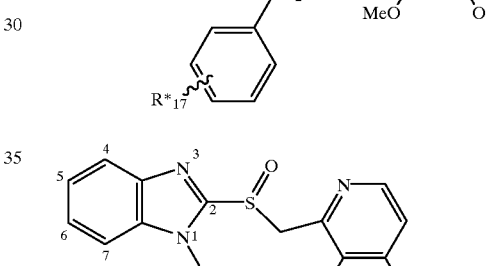

Formula 12

The most preferred groups for the $R_{19}R_{20}N$— combination in accordance with the present invention are dimethylamino, N-morpholino, and N-piperidinyl.

The most preferred compounds of the invention are those wherein the proton pump inhibitor portion is the same as in the widely used proton pump inhibitor drugs known under the names LANSOPRAZOLE, OMEPRAZOLE, PANTOPRAZOLE and RABEPRAZOLE and wherein the $R_{15}$ group is a benzenesulfonyl group mono-substituted either in the 4 (para) or in the 3 (meta) position with a Cl, Br, F, $CH_3$, $CH_3O$, $CF_3$, $CF_3O$—, $(CH_3)_2N$ or EtOCO group. These compounds are shown by Formulas 9, 10, 11 and 12, respectively, where $R_{17}^*$ represents said Cl, Br, F, $CH_3$, $CH_3O$, $CF_3$, $CF_3O$—, $(CH_3)_2N$ or EtOCO groups in the 4 (para) or in the 3 (meta) position of the phenyl ring, and where the numbering of the benzimidazole ring is shown in the formulas. In Formula 10 the $CH_3O$— group can occupy the 5 or the 6 position of the benzimidazole moiety, and in Formula 11 the $CF_2HO$— group can occupy the 5 or the 6 position of the benzimidazole moiety.

Examples of the presently most preferred compounds of the invention are as follows:
  1-benzenesulfonyl-5-methoxy-2-[(3,5-dimethyl-4-methoxy-2-pyridyl)methylsulfinyl]-1H-benzimidazole,
  1-benzenesulfonyl-6-methoxy-2-[(3,5-dimethyl-4-methoxy-2-pyridyl)methylsulfinyl]-1H-benzimidazole,
  1-benzenesulfonyl-5-difluoromethoxy-2-[(3,4-dimethoxy-2-pyridyl)methylsulfinyl]-1H-benzimidazole,
  1-benzenesulfonyl-6-difluoromethoxy-2-[(3,4-dimethoxy-2-pyridyl)methylsulfinyl]-1H-benzimidazole,
  1-benzenesulfonyl-2-[(3-methyl-4-(2',2',2'-trifluoroethoxy)-2-pyridyl)methylsulfinyl]-1H-benzimidazole,
  1-(p-chlorobenzenesulfonyl)-5-methoxy-2-[(3,5-dimethyl-4-methoxy-2-pyridyl)methylsulfinyl]-1H-benzimidazole,
  1-(p-chlorobenzenesulfonyl)-6-methoxy-2-[(3,5-dimethyl-4-methoxy-2-pyridyl)methylsulfinyl]-1H-benzimidazole, 1-(p-chlorobenzenesulfonyl)-5-difluoromethoxy-2-[(3,4-dimethoxy-2-pyridyl)methylsulfinyl]-1H-benzimidazole, 1-(p-chlorobenzenesulfonyl)-6-difluoromethoxy-2-[(3,4-dimethoxy-2-pyridyl)methylsulfinyl]-1H-benzimidazole, 1-(p-chlorobenzenesulfonyl)-2-[(3-methyl-4-(2',2',2'-trifluoroethoxy)-2-pyridyl)methylsulfinyl]-1H-benzimidazole, 1-(p-bromobenzenesulfonyl)-5-methoxy-2-[(3,5-dimethyl-4-methoxy-2-pyridyl)methylsulfinyl]-1H-benzimidazole, 1-(p-bromobenzenesulfonyl)-6-methoxy-2-[(3,5-dimethyl-4-methoxy-2-pyridyl)methylsulfinyl]-1H-benzimidazole, 1-(p-bromobenzenesulfonyl)-5-difluoromethoxy-2-[(3,4-dimethoxy-2-pyridyl)methylsulfinyl]-1H-benzimidazole, 1-(p-bromobenzenesulfonyl)-6-difluoromethoxy-2-[(3,4-dimethoxy-2-pyridyl)methylsulfinyl]-1H-benzimidazole, 1-(p-bromobenzenesulfonyl)-2-[(3-methyl-4-(2',2',2'-trifluoroethoxy)-2-pyridyl)methylsulfinyl]-1H-benzimidazole, 1-(p-fluorobenzenesulfonyl)-5-methoxy-2-[(3,5-dimethyl-4-methoxy-2-pyridyl)methylsulfinyl]-1H-benzimidazole, 1-(p-fluorobenzenesulfonyl)-6-methoxy-2-[(3,5dimethyl-4-methoxy-2 -pyridyl)methylsulfinyl]-1H-benzimidazole, 1-(p-fluorobenzenesulfonyl)-5-difluoromethoxy-2-[(3,4-dimethoxy-2-pyridyl)methylsulfinyl]-1H-benzimidazole, 1-(p-fluorobenzenesulfonyl)-6-difluoromethoxy-2-[(3,4-dimethoxy-2-pyridyl)methylsulfinyl]-1H-benzimidazole, 1-(p-fluorobenzenesulfonyl)-2-[(3-methyl-4-(2',2',2'-trifluoroethoxy)-2-pyridyl)methylsulfinyl]-1H-benzimidazole, 1-(p-methylbenzenesulfonyl)-5-methoxy-2-[(3,5-dimethyl-4-methoxy-2-pyridyl)methylsulfinyl]-1H-benzimidazole, 1-(p-methylbenzenesulfonyl)-6-methoxy-2-[(3,5-dimethyl-4-methoxy-2-pyridyl)methylsulfinyl]-1H-benzimidazole, 1-(p-methylbenzenesulfonyl)-5-difluoromethoxy-2-[(3,4-dimethoxy-2-pyridyl)methylsulfinyl]-1H-benzimidazole, 1-(p-methylbenzenesulfonyl)-6-difluoromethoxy-2-[(3,4-dimethoxy-2-pyridyl)methylsulfinyl]-1H-benzimidazole, 1-(p-methylbenzenesulfonyl)-2-[(3-methyl-4-(2',2',2-trifluoroethoxy)-2-pyridyl)methylsulfinyl]-1H-benzimidazole, 1-(p-methoxybenzenesulfonyl)-5-methoxy-2-[(3,5-dimethyl-4-methoxy-2-pyridyl)methylsulfinyl]-1H-benzimidazole, 1-(p-methoxybenzenesulfonyl)-6-methoxy-2-[(3,5-dimethyl-4-methoxy-2-pyridyl)methylsulfinyl]-1H-benzimidazole, 1-(p-methoxybenzenesulfonyl)-5-difluoromethoxy-2-[(3,4-dimethoxy-2-pyridyl)methylsulfinyl]-1H-benzimidazole, 1-(p-methoxybenzenesulfonyl)-6-difluoromethoxy-2-[(3,4-dimethoxy-2-pyridyl)methylsulfinyl]-1H-benzimidazole, 1-(p-methoxybenzenesulfonyl)-2-[(3-methyl-4-(2',2'-trifluoroethoxy)-2-pyridyl)methylsulfinyl]-1H-benzimidazole, 1-(3-trifluoromethylbenzenesulfonyl)-5-methoxy-2-[(3,5-dimethyl-4-methoxy-2-pyridyl)methylsulfinyl]-1H-benzimidazole, 1-(3-trifluoromethylbenzenesulfonyl)-6-methoxy-2-[(3,5-dimethyl-4-methoxy-2-pyridyl)methylsulfinyl]-1H-benzimidazole, 1-(3-trifluoromethylbenzenesulfonyl)-5-difluoromethoxy-2-[(3,4-dimethoxy-2-pyridyl)methylsulfinyl]-1H-benzimidazole, 1-(3-trifluoromethylbenzenesulfonyl)-6-difluoromethoxy-2-[(3,4-dimethoxy-2-pyridyl)methylsulfinyl]-1H-benzimidazole, 1-(3-trifluoromethylbenzenesulfonyl)-2-[(3-methyl-4-(2',2',2'-trifluoroethoxy)-2-pyridyl)methylsulfinyl]-1H-benzimidazole, 1-(p-trifluoromethoxybenzenesulfonyl)-5-methoxy-2-[(3,5-dimethyl-4-methoxy-2-pyridyl)methylsulfinyl]-1H-benzimidazole, 1-(p-trifluoromethoxybenzenesulfonyl)-6-methoxy-2-[(3,5-dimethyl-4-methoxy-2-pyridyl)methylsulfinyl]-1H-benzimidazole, 1-(p-trifluoromethoxybenzenesulfonyl)-5-difluoromethoxy-2-[(3,4-dimethoxy-2-pyridyl)methylsulfinyl]-1H-benzimidazole, 1-(p-trifluoromethoxybenzenesulfonyl)-6-difluoromethoxy-2-[(3,4-dimethoxy-2-pyridyl)methylsulfinyl]-1H-benzimidazole, 1-(p-trifluoromethoxybenzenesulfonyl)-2-[(3-methyl-4-(2',2',2'-trifluoroethoxy)-2-pyridyl)methylsulfinyl]-1H-benzimidazole, 1-(p-dimethylaminobenzenesulfonyl)-5-methoxy-2-[(3,5-dimethyl-4-methoxy-2-pyridyl)methylsulfinyl]-1H-benzimidazole, 1-(p-dimethylaminobenzenesulfonyl)-5-difluoromethoxy-2-[(3,4-dimethoxy-2-pyridyl)methylsulfinyl]-1H-benzimidazole, 1-(p-dimethylaminobenzenesulfonyl)-2-[(3-methyl-4-(2',2',2'-trifluoroethoxy)-2-pyridyl)methylsulfinyl]-1H-benzimidazole, 1-(p-ethoxycarbonylbenzenesulfonyl)-5-methoxy-2-[(3,5-dimethyl-4-methoxy-2-pyridyl)methylsulfinyl]-1H-benzimidazole, 1-(p-ethoxycarbonylbenzenesulfonyl)-2-[(3-methyl-4-(2',2',2'-trifluoroethoxy)-2-pyridyl)methylsulfinyl]-1H-benzimidazole.

The compounds of the invention wherein the $R_{15}$ group is an arylsulfonyl group, can be prepared by the reacting the 2-pyridylmethylsulfinyl-1H-benzimidazole derivatives (or structurally related compounds) having a free NH group within the imidazole moiety, with an arylsulfonyl chloride. In the broad sense the benzimidazole or structurally related compound which is the starting material having the free NH group, can be described by Formula 1 wherein the $R_{15}$ group would be H. Similarly, in the broad sense the arylsulfonyl chloride reagent is described by the formula $R_{21}(R_{17})SO_2Cl$ where the $R_{21}$ and $R_{17}$ groups are defined as in connection with Formula 1. Reaction Scheme 1 discloses a process for preparing examplary preferred compounds of the invention by reacting the 2-pyridylmethylsulfinyl-1H-benzimidazole derivative of Formula 13 with a benzenesulfonyl chloride derivative of Formula 14 in the presence of a suitable base. The reaction is typically conducted in an inert organic solvent, such as dichloromethane in the presence of an organic base, such as triethylamine. For compounds of Formula 13 and Formula 14 the $R_1$–$R_3$, $R_6$–$R_9$ and $R_{17}$ groups are defined as in connection with Formula 1. As it can be seen in Reaction Scheme 1, the benzenesulphonylation reaction may give rise to two isomeric or tautomeric products depending on the nature and positions of the $R_6$–$R_9$ substituents on the benzimidazole ring. The two isomeric products (which may be merely taumers) are shown in Formulas 15 and 16.

The benzenesulfonyl chloride derivatives of Formula 14 can be obtained in accordance with procedures well known in the art.

the reagent of Formula 14, to react with the compounds of Formula 13. The reagent of the formula $R_{21}(C_6H_4)S(O)(Cl)NR_{16}$ can be obtained in accordance with methods known in the art, for example as described in the treatise COMPREHENSIVE ORGANIC FUNCTIONAL GROUP TRANSFORMATIONS, Volume 7, Editors-in-Chief A. R. Katritzky, O. Meth-Cohn and C. W. Rees (Pergamon).

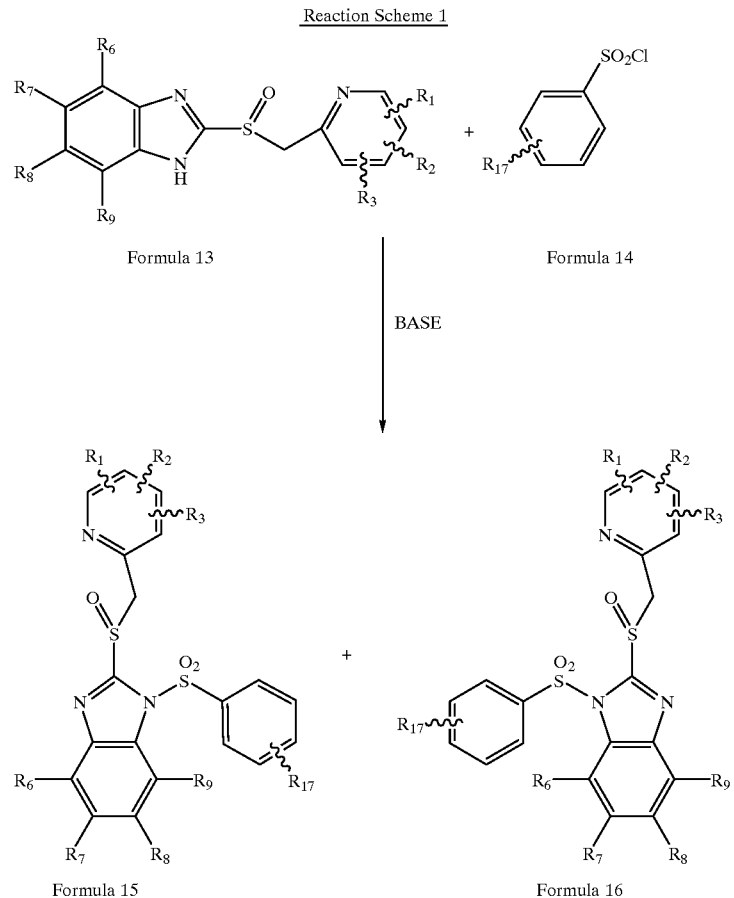

Reaction Scheme 1

Formula 13

Formula 14

BASE

Formula 15

Formula 16

Those skilled in the art will recognize the 2-pyridylmethylsulfinyl-1H-benzimidazole derivatives of Formula 13 as the proton pump inhibitors generally known in the art and described for example in U.S. Pat. No. 4,686,230 (Rainer et. al.) and in published international application WO 97/48380 (Astra Aktiobiolag). Starting materials within the scope of Formula 13 include the known drugs LANSOPRAZOLE (U.S. Pat. No. 4,628,098), OMEPRAZOLE (U.S. Pat. No. 4,255,431), PANTOPRAZOLE (U.S. Pat. No. 4,758,579) and RABEPRAZOLE (U.S. Pat. No. 5,045,552) Thus, the starting compounds of Formula 13 can be prepared in accordance with the state-of-the-art, for example as described in U.S. Pat. Nos. 4,686,230, 4,628,098, 4,255,431, 4,758,579, 5,045,552 and international application WO 97/48380, all of which are specifically incorporated herein by reference.

Although this is not shown in the reaction scheme, to obtain compounds of the invention where with reference to Formula 1 $R_{15}$ is $R_{21}(C_6H_4)SOY$ and Y is $=NR_{16}$, a reagent of the formula $R_{21}(C_6H_4)S(O)(Cl)NR_{16}$ is used instead of Instead of using the free benzimidazole compounds of Formula 13, their suitable salts such as the sodium, potassium, magnesium (and other) salts can be reacted with the benzenesulfonyl chloride derivative of Formula 13, to also provide the exemplary compounds of the invention in accordance with Formulas 15 and 16.

Reaction Scheme 2 discloses an alternative method for preparing the exemplary compounds of the invention, shown in Formulas 15 and 16. This reaction involves the oxidation of the corresponding 1-(N)-benzenesulfonyl-benzimidazolyl, 2-pyridylmethyl sulfide compounds of Formulas 17 and 18 to the corresponding sulfoxides. Those skilled in the art will recognize that Formulas 17 and 18 represent isomeric compounds which may be different or identical (tautomeric) with one another depending on the nature and position of the $R_6$–$R_9$ substituents. The oxidation reaction can be performed with oxidizing agents known in the art for forming sulfoxides, for example hydrogen peroxide, m-chloroperoxybenzoic acid and iodosobenzene may serve for this purpose. The oxidation reaction is normally conducted in an aprotic neutral solvent, such as dichloromethane. The disulfide compounds of Formulas 17 and 18 can be obtained by performing a benzenesulphonylation reaction (in analogy to the reaction of Scheme 1) on the disulfide compounds having a free benzimidazole NH group, or their suitable salt. The latter disulfides (Formulas 17 and 18) can be obtained in accordance with the state-of-the-art.

structurally related compounds) form a Mannich base, can be made under conditions which are generally applicable and known in the art for forming Mannich bases. A specific detailed description for forming Mannich base type prodrugs is provided by Bundgaard et al. in *Methods in Enzymology* 112, p347–359 which is incorporated herein by reference. Generally speaking, the preparation of Mannich base type Reaction Scheme 2

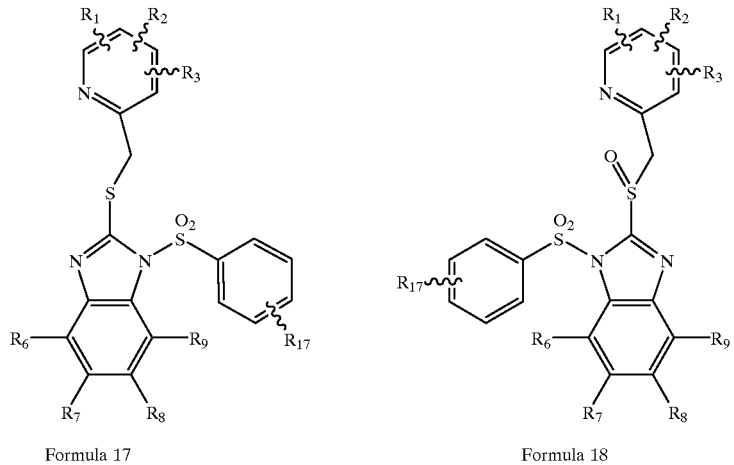

Formula 17          Formula 18

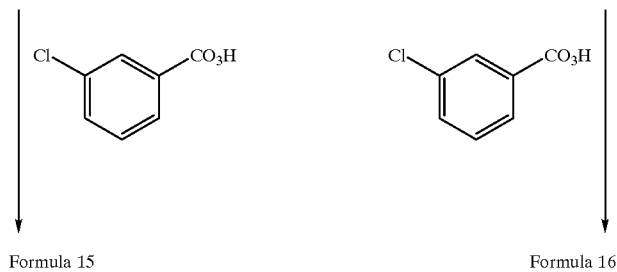

Formula 15          Formula 16

The compounds of the invention where the physiologically labile $R_{15}$ group is $R_{16}(R_{17})SO$ (sulfinyl), as defined in connection with Formula 1, can be made in reactions which are analogous to the reactions shown in Scheme 1, except that instead of an arylsulfonyl chloride an arylsulfinyl chloride of formula $R_{16}(R_{17})SOCl$ is used. The arylsulfinylation reaction is usually conducted in the presence of an organic base, in a solvent such as dioxane, tetrahydrofuran, or an alcohol. The arylsulfinyl chloride of formula $R_{16}(R_{17})SOCl$ can be made from the corresponding sulfinic acid or salt having the formula $R_{16}(R_{17})SO_2Na$, by treatment with thionyl chloride. In view of their close analogy to the sulfonylation reactions of Scheme 1, the sulfinylation reactions are not shown in a scheme.

The compounds of the invention where the physiologically labile $R_{15}$ group together with the 2-pyridylmethylsulfinyl-1H-benzimidazole derivatives (or prodrugs of this invention involves heating a mixture of an amine of the formula $R_{19}R_{20}NH$ with an aldehyde or ketone of the formula $OC(R_{18})_2$ in an alcohol, water, dioxane or other suitable solvent. The symbols $R_{18}$–$R_{20}$ are defined as in connection with Formula 1.

Reaction Scheme 3 illustrates the preparation of exemplary Mannich base type compounds of the invention from the 2-pyridylmethylsulfinyl-1H-benzimidazole derivatives of Formula 13 using formaldehyde as the aldehyde and dimethylamine as the amine. As it can be seen in the reaction scheme, this reaction also may provide two isomeric products of Formula 19 and 20, respectively. The two products may be identical (tautomeric) depending on the nature and position of the $R_6$–$R_9$ substituents.

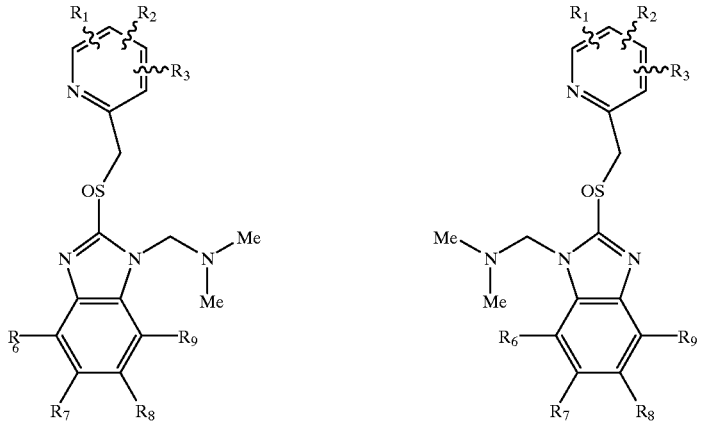

Reaction Scheme 3

A significant advantage of the compounds of the present invention is that they can release the active forms of the proton pump inhibitors spontaneously by hydrolysis in the mammalian (including human) body. Hydrolysis can occur chemically or enzymatically. Because the compounds of this invention spontaneously release the active form of the proton pump inhibitor drugs by in vivo hydrolysis, they can attain longer duration of effective drug concentration in the body. Thus, the compounds of the present invention are prodrugs which are converted to active drugs by hydrolysis in the body, providing long duration of effective concentration. The long duration of inhibitory activity by spontaneous hydrolysis of the compounds of this invention allows more effective inhibition of gastric acid secretion, which enables better therapy of acid related disease as defined on p.1. and p.2. Compounds of this invention can be administered for inhibiting gastric acid secretion orally. The typical daily dose of the compounds will depend on various factors such as the individual requirement of each patient. In general, oral and parenteral dosages will be in the range of 5 to 100 mg per day.

Those skilled in the art will readily understand that for oral administration the compounds of the invention are admixed with pharmaceutically acceptable excipients which per se are well known in the art. Specifically, a drug to be administered systemically, it may be confected as a powder, pill, tablet or the like or as a syrup or elixir suitable for oral administration. Description of the subtances normally used to prepare tablets, powders, pills, syrups and elixirs can be found in several books and treatise well known in the art, for example in Remington's Pharmaceutical Science, Edition 17, Mack Publishing Company, Easton, Pa.

Compounds of the present invention can be combined with certain amounts of known proton pump inhibitors, e. g. LANSOPRAZOLE, OMEPRAZOLE, PANTOPRAZOLE, or RABEPRAZOLE, to provide a drug-prodrug combination, and the combination administered for inhibition of gastric acid secretion. Thus, initially the proton pump inhibitor (drug) inhibits gastric acid secretion of the patient. The aforesaid known and widely used proton pump inhibitors have 60–90 minutes of plasma half-life. As the effective concentration of the proton pump inhibitor (drug) is decreased by metabolism, the compounds of the present invention (prodrug) continuosly undergoes hydrolysis and provides and maintains new active inhibitor concentration in the mammalian, including human body.

A disadvantage of the presently used proton pump inhibitors is that for therapy by injection in a liquid form they must be reconstituted from a lyophilized powder in a medium having the high pH of approximately 9.5. The prodrugs of the present invention overcome the disadvantage of requiring a reconstituting medium having such high pH, because the compounds of the present invention can be reconstituted to form an injectable liquid in a medium of approximately pH 6.0 to 8.5. It will be readily appreciated by those skilled in the art that for administration in liquid form by injection the liquid that reconstitues the drug is a pharmaceutically acceptable aqueous solution that per se is known in the art. Such pharmaceutically acceptable solutions utilized for administration of drugs in injectable form are described for example in the treatise PHARMACEUTICAL DOSAGE FORMS (Parenteral Medications, Volume 1, Edited by K. E. Avis, H. A. Lieberman and L. Lachman (1992).

Among the benefits of the pre-proton pump inhibitor (P-PPI) type of drugs of the present invention is their ability to provide more effective treatment of errosive esophagitis and of less severe reflux diseases as well. This is because effective treatment of errosive esophagitis (and to a lesser extent of lesser reflux diseases) requires prevention of the reflux of gastric contents at pH 3.0 or still lower pH. The current PPI drugs allow several acidic excursions to pH<2.0 per day, resulting in a moderate to weak amelioration of symptoms. 5 However, healing would require elevation to pH>4.0 for about 16 hours per day or longer. When, as in current usual treatment by PPIs, the other 8 hours contain episodic acidity to pH 3.0 or less, the patients tend to continue to complain of pain. The more effective and more continues acid suppression by the drugs of the present invention is likely to result in substantially better treatment of this disease, as well as faster healing of all acid related erosions or ulcers.

The pre-proton pump inhibitor (P-PPI) type of drugs of the present invention provide improved dual therapy for *H. pylori* eradication. This is because the PPI's synergize with cell division dependent antibiotics such as amoxicillin (cell wall biosynthesis) and clarithromycin (protein synthesis) by elevating gastric surface pH to enable a larger fraction of the bacterial population to be in dividing phase during presentation of the antibiotic to the gastric lumen. However, their effect on intragastric pH is limited by their dwell time in the plasma. The pre-proton pump inhibitor (P-PPI) type of drugs of the present invention can continuosly elevate intragastric pH close to neutrality on current once a day therapy. Therefore, 100% eradication of the bacteria is expected in dual therapy with the prodrugs of the invention (for example a pro-drug of OMEPRAZOLE in accordance with the invention) plus an effective antibiotic, such as amoxicillin.

Even monotherapy for *H. pylori* eradication is likely to be successful with the pre-proton pump inhibitor (P-PPI) type of drugs of the present invention. This is because in the absence of acid, the enzyme *H. pylori* urease elevates environmental pH to >8.3, which is toxic to the organism. PPI's in current formulation inhibit growth or present of the organism in the antrum, due to elevation of antral pH to close to neutrality. Elevation of 24 hour pH to neutrality, as it can be accomplished with the drugs of the present invention, is likely to result in "self eradication" of the bacteria.

Approximately 30% of patients with gastrointestinal distress appear with symptoms without quantitative underlying disease (non-ulcer dyspepsia). The most likely cause for these symptoms is upper gastrointestinal afferent nerve sensitivity to gastric acid. Only acid ablation ameliorates these symptoms and this can be attained with the drugs of the present invention.

By way of concrete examples, the following tests and results are described. Certain compounds of the invention have been tested in one or more standard laboratory tests that demonstrate gastric antisecretory activity. The compounds of the invention did not directly inhibit the K+-dependent ATP hydrolysis of gastric H,K-ATPase. However, after hydrolysis the compounds of this invention showed strong inhibition of gastric H,K-ATPase activity. This is consistent with the knowledge that the compounds obtained by hydrolysis e. g. LANSOPRAZOLE, OMEPRAZOLE, PANTOPRAZOLE and RABEPRAZOLE are well known H,K-ATPase inhibitors. For example, 1-benzenesulfonyl-5-methoxy-2-[(3,5-dimethyl-4-methoxy-2-pyridyl)methylsulfinyl]-1H-benzimidazole was tested for inhibitory activity of gastric H,K-ATPase. Initially this compound did not inhibit gastric H,K-ATPase. However, gastric H,K-ATPase activity was spontaneously inhibited as hydrolysis of this compound in aqueous solution at pH 7.4 proceeded. After 5.75 hr—hydrolysis at pH 7.4, this compound inhibited 91% of gastric H,K-ATPase activity, same as 5-methoxy-2-[(3,5-dimethyl-4-methoxy-2-pyridyl)methylsulfinyl]-1H-benzimidazole (OMEPRAZOLE) which was the product of the hydrolysis. It was determined that 1-benzenesulfonyl-5-methoxy-2-[(3,5-dimethyl-4-methoxy-2-pyridyl)methylsulfinyl]-1H-benzimidazole was hydrolyzed to 5-methoxy-2-[(3,5-dimethyl-4-methoxy-2-pyridyl)methylsulfinyl]-1H-benzimidazole (OMEPRAZOLE) with a half-life ($t_{1/2}$) 3×0.5 hr at 37° C. at pH 7.4.

SPECIFIC EMBODIMENTS AND EXPERIMENTAL DESCRIPTION

EXAMPLE 1

1-Benzenesulfonyl-5-methoxy-2-[(3,5-dimethyl-4-methoxy-2-pyridyl)methylsulfinyl]-1H-benzimidazole Method A: 5-Methoxy-2-[(3,5-dimethyl-4-methoxy-2-pyridyl)methylsulfinyl]-1H-benzimidazole(172 mg, 0.5 mmole) was dissolved in 20 ml of dichloromethane and 0.140 ml of triethylamine. The solution was cooled to 0–4° C. in an ice bucket. Benzenesulfonyl chloride (96 mg, 0.55 mmole) was slowly added and stirred at 0–4° C. with thin layer chromatography monitoring (developing solvent system: chloroform-methanol (10:1) and acetonitrile-chloroform (1:1)). After the reaction was complete, the organic layer was washed with an aqueous solution composed of 0.1M NaCl, and 0.1M sodium phosphate, pH 8.5. The organic layer was dried over anhydrous magnesium sulfate and concentrated under reduced pressure. The residual material was crystallized from dichloromethane-ethyl ether-heptane to provide 127 mg of product. M. p. 87–89° C. (decomposition). Heptane was introduced to the remaining organic layer to provide a second crop of product (104 mg). After combining the solids, 231 mg of the product (yield 95%) was obtained.

1H NMR (CDCl3, δ: 8.10-8.15 (m, 2H), 7.45-7.80(m, 5H), 7.26(s, 1H), 7.0-7.1(m, 1H), 4.8-5.0(q, 2H), 3.92(s, 3H), 3.75(s, 3H), 2.31(s, 3H), 2.23(s, 3H)

Method B: A mixture of 1-benzenesulfonyl-5-methoxy-2-[(3,5-dimethyl- 4-methoxy-2-pyridyl)methylthio]-1H-benzimidazole and 1-benzenesulfonyl-6-methoxy-2-[(3,5-dimethyl-4-methoxy-2-pyridyl)methylthio]-1H-benzimidazole was prepared by reacting 5-methoxy-2-[(3,5-dimethyl-4-methoxy-2-pyridyl)methylthio]-1H-benzimidazole with benzenesulfonyl chloride as in method A. 1-Benzenesulfonyl-5-methoxy-2-[(3,5-dimethyl-4-methoxy-2-pyridyl)methylthio]-1H-benzimidazole was isolated by silica gel column chromatography and used in the next step as follows. 1-Benzenesulfonyl-5-methoxy-2-[(3,5-dimethyl-4-methoxy-2-pyridyl)methylthio]-1H-benzimidazole (318 mg, 1 mmole) in 30 ml of dichloromethane was cooled to −20° C. A dichloromethane solution (5 ml) containing m-chloroperbenzoic acid (equivalent to 1 mmole from 60% purity) was slowly added. The reaction was monitored by thin layer chromatography. After 5 hours the organic layer was washed with an aqueous solution of 0.1M sodium bicarbonate and 50 mM sodium thiosulfate. The organic layer was dried over anhydrous magnesium sulfate and concentrated under reduced pressure. Residual material was solidified from dichloromethane-ethyl ether-heptane to provide 397 mg of product (yield 82%), 1-benzenesulfonyl-5-methoxy-2-[(3,5-dimethyl-4-methoxy-2-pyridyl)methylsulfinyl]-1H-benzimidazole.

EXAMPLES 2–19

The compounds listed under Examples 2–19 below were prepared using the method A as described in Example 1. 2-Pyridylmethylsulfinyl benzimidazole compounds were reacted with the corresponding arylsulfonyl chloride to give the corresponding 1-arylsulfonyl-2-pyridylmethylsulfinyl benzimidazoles as shown in Table 1 with reference to Formula 21.

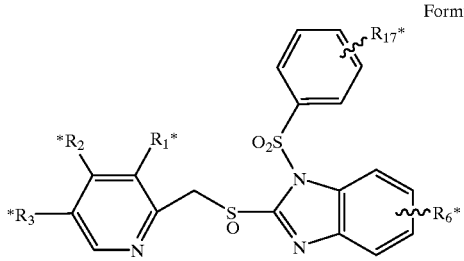

Formula 21

TABLE 1

| # | $R_6$* | $R_1$* | $R_2$* | $R_3$* | $R_{17}$* | Yield (%) | m.p. (° C.) |
|---|---|---|---|---|---|---|---|
| 2 | 5-OCH$_3$ | —CH$_3$ | —OCH$_3$ | —CH$_3$ | 4-Cl | 81 | 76–78 |
| 3 | 5-OCH$_3$ | —CH$_3$ | —OCH$_3$ | —CH$_3$ | 4-Br | 73 | 84–86 |
| 4 | 5-OCH$_3$ | —CH$_3$ | —OCH$_3$ | —CH$_3$ | 4-F | 85 | 70–72 |
| 5 | 5-OCH$_3$ | —CH$_3$ | —OCH$_3$ | —CH$_3$ | 4-CH$_3$ | 79 | 64–66 |
| 6 | 5-OCH$_3$ | —CH$_3$ | —OCH$_3$ | —CH$_3$ | 4-OCH$_3$ | 83 | 85–87 |
| 7 | 5-OCH$_3$ | —CH$_3$ | —OCH$_3$ | —CH$_3$ | 3-CF$_3$ | 67 | 65–67 |
| 8 | 5-OCH$_3$ | —CH$_3$ | —OCH$_3$ | —CH$_3$ | 4-OCF$_3$ | 78 | 63–64 |
| 9 | H | —CH$_3$ | OCH$_2$CF$_3$ | H | H | 78 | 80–83 |
| 10 | H | —CH$_3$ | OCH$_2$CF$_3$ | H | 4-Cl | 79 | 90–92 |
| 11 | H | —CH$_3$ | OCH$_2$CF$_3$ | H | 4-Br | 71 | 105–107 |
| 12 | H | —CH$_3$ | OCH$_2$CF$_3$ | H | 4-F | 73 | 85–87 |
| 13 | H | —CH$_3$ | OCH$_2$CF$_3$ | H | 4-CH$_3$ | 67 | 125–126 |
| 14 | H | —CH$_3$ | OCH$_2$CF$_3$ | H | 4-OCH$_3$ | 78 | 94–95 |
| 15 | H | —CH$_3$ | OCH$_2$CF$_3$ | H | 3-CF$_3$ | 67 | 123–125 |
| 16 | H | —CH$_3$ | OCH$_2$CF$_3$ | H | 4-OCF$_3$ | 78 | 125–126 |
| 17 | 5-OCHF$_2$ | OCH$_3$ | OCH$_3$ | H | H | 92 | 51–54 |
| 18 | 5-OCHF$_2$ | OCH$_3$ | OCH$_3$ | H | 4-OCH$_3$ | 87 | 67–69 |
| 19 | 5-OCHF$_2$ | OCH$_3$ | OCH$_3$ | H | 4-OCF$_3$ | 87 | 61–63 |

EXAMPLE 20

5-Difluoromethoxy-2-[(3,4-dimethoxy-2-pyridyl) methylsulfinyl]-1H-benzimidazole, sodium salt sesquihydrate (432 mg, 1 mmole) was suspended in 30 ml of dichloromethane in the presence of anhydrous sodium carbonate (100 mg). 4-Chlorobenzenesulfonyl chloride (211 mg, 1 mmole) was added to the suspension and stirred at 4° C. overnight. The organic layer was separated by filtration and concentrated under reduced pressure. The residual solid was crystallized from dichloromethane-ethyl ether-heptane. 417 mg of 1-(4-chlorobenzenesulfonyl)-5-difluoromethoxy-2- [(3,4-dimethoxy-2-pyridyl) methylsulfinyl]-1H-benzimidazole was obtained. Yield 74.5%.
M.P. 82–83° C.
1H NMR (CDCl3, δ: 8.05-8.15(m, 2H), 8.0(d, 1H), 7.78-7.81(m, 1H), 7.45-7.6(m, 2H), 7.2-7.3(m, 1H), 6.80-6.81(d, 1H1), 6.5-6.6(d, 1H), 4.9-5.0(q, 2H), 3.93(s, 3H), 3.90(s, 3H), 3.5(q, 1H)

EXAMPLES 21–24

The compounds listed in Table 2, with reference to Formula 20, were prepared using the method described in Example 20.

TABLE 2

| % | $R_6$* | $R_1$* | $R_2$* | $R_3$* | $R_{17}$* | Yield (%) | m.p.(° C.) |
|---|---|---|---|---|---|---|---|
| 21 | 5-OCHF$_2$ | OCH$_3$ | OCH$_3$ | H | 4-Br | 87 | 80–82 |

TABLE 2-continued

| % | $R_6$* | $R_1$* | $R_2$* | $R_3$* | $R_{17}$* | Yield (%) | m.p.(° C.) |
|---|---|---|---|---|---|---|---|
| 22 | 5-OCHF$_2$ | OCH$_3$ | OCH$_3$ | H | 4-F | 78 | 67–70 |
| 23 | 5-OCHF$_2$ | OCH$_3$ | OCH$_3$ | H | 4-CH$_3$ | 88 | 73–75 |
| 24 | 5-OCHF$_2$ | OCH$_3$ | OCH$_3$ | H | 3-CF$_3$ | 83 | 62–66 |

CHEMICAL STABILITY

The chemical stability of the compounds of the invention has been followed kinetically at low concentration at 37° C. in a buffer solution composed of 0.2M NaCl, 50 mM sodium phosphate, pH 7.4, 2% bovine albumin serum, 5–10% methanol. The compounds of Example 1 and Example 19 were measured to have a half-life ($t_{1/2}$) 3 hr ±0.5 hr and 3.5 hr ±0.3 hr, respectively. The compound of Example 1 has slightly higher solubility in aqueous buffer than the compound of Example 19. The solubility of these compounds was found to affect their rate of hydrolysis.
Acid stability of the compounds was assayed in 95% methanol containing 0.1N HCl. Approximately 90% of the compound of Example 1 was still present intact (without decomposition) after 2.25 hour in this solution.

BIOLOGICAL ASSAY

Inhibition of ATPase activity was measured using isolated hog gastric vesicles. The gastric H,K-ATPase (10 μg) was incubated at 37° C. in a solution (1 ml) composed of 0.25M sucrose, 20 mM Pipes/Tris, pH 7.4, 0.15M KCl, 2 mM MgCl$_2$, valinomycin 2 μg/ml, and various concentration of compounds of the invention. At timed intervals, ATP was added (up to 2 mM) and incubated for 15 minutes and amount of released phosphate ion was measured. As a control experiment the prior art drug without a labile group on the benzimidazole nitrogen (e. g. OMEPRAZOLE or LANSOPRAZOLE) was used for measuring inhibition of enzyme activity. Initially (before it underwent hydrolysis), the samples having 10, 20, 50, and 100 μM of the compound of Example 1 failed to inhibit enzyme activity. After 80 minutes however, the sample having 10 μM of the compound of Example 1 inhibited 10% and the sample having 50 μM inhibited 50%. In samples having 10 μM of OMEPRAZOLE (control) and 10 μM of the compound of Example 1, the same level of inhibition was obtained after 5.75 hours of hydrolysis.

What is claimed is:

1. A compound of the formula

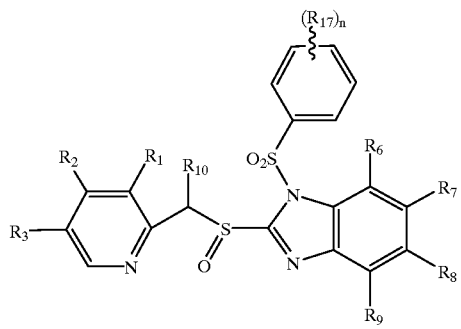

where $R_1$, $R_2$ and $R_3$ are independently selected from hydrogen, alkyl of 1 to 10 carbons, fluoro substituted alkyl of 1 to 10 carbons, alkoxy of 1 to 10 carbons, fluoro substituted alkoxy of 1 to 10 carbons, alkylthio of 1 to 10 carbons, fluoro substituted alkylthio of 1 to 10 carbons, alkoxyalkoxy of 2 to 10 carbons, amino, alkylamino and dialkylamino each of the alkyl groups in said alkylamino and dialkyl amino groups having 1 to 10 carbons, halogen, phenyl, alkyl substituted phenyl, alkoxy substituted phenyl, phenylalkoxy, each of the alkyl groups in said alkyl substituted phenyl, alkoxy substituted phenyl and phenylalkoxy having 1 to 10 carbons, piperidino, morpholino or two of the $R_1$, $R_2$ and $R_3$ groups jointly forming a 5 or 6 membered ring having 0 or 1 heteroatom selected from N, S and O;

$R_6$ through $R_9$ are independently selected from hydrogen, alkyl of 1 to 10 carbons, halogen substituted alkyl of 1 to 10 carbons, alkoxy of 1 to 10 carbons, halogen substituted alkoxy of 1 to 10 carbons, alkylcarbonyl, alkoxycarbonyl, the alkyl group in said alkylcarbonyl and alkoxycarbonyl having 1 to 10 carbons, oxazolyl, imidazolyl, thiazolyl, pyrazolyl, or any two adjacent ones of the $R_6$ through $R_9$ groups may form a ring that may optionally include a heteroatom selected from N, 0 and S and said ring may be further substituted;

$R_{10}$, is hydrogen, alkyl of 1 to 10 carbons, or $R_{10}$ may form an alkylene chain together with $R_3$;

$R_{17}$ is alkyl of 1 to 10 carbons, halogen substituted alkyl of 1 to 10 carbons, alkoxy having 1 to 10 carbons, halogen substituted alkoxy of 1 to 10 carbons, alkylthio having 1 to 10 carbons, halogen substituted alkylthio of 1 to 10 carbons, alkoxy carbonyl having 1 to 10 carbons, halogen substituted alkoxy carbonyl having 1 to 10 carbons, F, Cl, Br, I, $NO_2$, CN, OCOalkyl, $NH_2$, alkylamino and dialkylamino where in said OCOalkyl,, alkylamino and dialkylamino groups each of said alkyl group has 1 to 10 carbons, and n is an integer having the value 0 to 5.

2. A compound in accordance with claim 1 which is 1-(p-dimethylaminobenzenesulfonyl)-5-methoxy-2-[(3,5-dimethyl-4-methoxy-2-pyridyl)methylsulfinyl]-1H-benzimidazole.

3. A compound of the formula

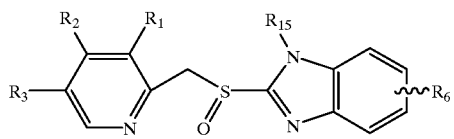

wherein $R_1$ is methyl or methoxy;

$R_2$ is methoxy or 2,2,2-trifluoroethoxy;

$R_3$ is H or methyl, and $R_6$ is H, methoxy or difluoromethoxy group in the 5 or in the 6 position of the benzimidazole moiety;

$R_{15}$ is

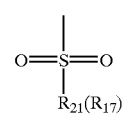

where $R_{17}$ is alkyl of 1 to 10 carbons, halogen substituted alkyl of 1 to 10 carbons, alkoxy having 1 to 10 carbons, halogen substituted alkoxy of 1 to 10 carbons, alkylthio having 1 to 10 carbons, halogen substituted alkylthio of 1 to 10 carbons, alkoxy carbonyl having 1 to 10 carbons, halogen substituted alkoxy carbonyl having 1 to 10 carbons, F, Cl, Br, I, $NO_2$, CN, OCOalkyl, $NH_2$, alkylamino and dialkylamino where in said OCOalkyl,, alkylamino and dialkylamino groups each of said alkyl group has 1 to 10 carbons;

$R_{21}$ is phenyl, naphthyl or heteroaryl having 1 to 3 heteroatoms independently selected from N, O and S, said phenyl, naphthyl or heteroaryl groups being unsubstituted or substituted with 1 to 5 $R_{17}$ groups, or to a pharmaceutically acceptable salt of said compound.

4. A compound in accordance with claim 1 where $R_{17}$ is selected from Cl, Br, F, lower alkyl, lower alkoxy, trifluoromethyl, trifluoromethoxy, di-(lower alkyl)amino, and lower alkoxycarbonyl.

5. A compound in accordance with claim 1 where $R_{17}$ is selected from Cl, Br, F, methyl, methoxy, trifluoromethyl, trifluoromethoxy, dimethylamino and ethoxycarbonyl.

6. A compound in accordance with claim 2, selected from the group consisting of:

1-benzenesulfonyl-5-methoxy-2-[(3,5-dimethyl-4-methoxy-2-pyridyl)methylsulfinyl]-1H-benzimidazole, 1-benzenesulfonyl-6-methoxy-2-[(3,5-dimethyl-4-methoxy-2-pyridyl)methylsulfinyl]-1H-benzimidazole, 1-benzenesulfonyl-5-difluoromethoxy-2-[(3,4-dimethoxy-2-pyridyl)methylsulfinyl]-1H-benzimidazole, 1-benzenesulfonyl-6-difluoromethoxy-2-[(3,4-dimethoxy-2-pyridyl)methylsulfinyl]-1H-benzimidazole, 1-benzenesulfonyl-2-[(3-methyl-4-(2',2',2'-trifluoroethoxy)-2-pyridyl)methylsulfinyl]-1H-benzimidazole, 1-(p-chlorobenzenesulfonyl)-5-methoxy-2-[(3,5-dimethyl-4-methoxy-2-pyridyl)methylsulfinyl]-1H-benzimidazole, 1-(p-chlorobenzenesulfonyl)-6-methoxy-2-[(3,5-dimethyl-4-methoxy-2-pyridyl)methylsulfinyl]-1H-benzimidazole, 1-(p-chlorobenzenesulfonyl)-5-difluoromethoxy-2-[(3,4-dimethoxy-2-pyridyl)methylsulfinyl]-1H-benzimidazole, 1-(p-chlorobenzenesulfonyl)-6-difluoromethoxy-2-[(3,4-dimethoxy-2-pyridyl)methylsulfinyl]-1H-benzimidazole, 1-(p-chlorobenzenesulfonyl)-2-[(3-methyl-4-(2',2',2'-trifluoroethoxy)-2-pyridyl)methylsulfinyl]-1H-benzimidazole, 1-(p-bromobenzenesulfonyl)-5-methoxy-2-[(3,5-dimethyl-4-methoxy-2-pyridyl)methylsulfinyl]-1H-benzimidazole, b  1-(p-bromobenzenesulfonyl)-6-methoxy-2-[(3,5-dimethyl-4-methoxy-2-pyridyl)methylsulfinyl]-1H-benzimidazole, 1-(p-bromobenzenesulfonyl)-5-difluoromethoxy-2-[(3,4-dimethoxy-2-pyridyl)methylsulfinyl]-1H-benzimidazole, 1-(p-bromobenzenesulfonyl)-6-difluoromethoxy-2-[(3,4-dimethoxy-2-pyridyl)methylsulfinyl]-1H-benzimidazole, 1-(p-bromobenzenesulfonyl)-2-[(3-methyl-4-(2',2',2'-trifluoroethoxy)-2-pyridyl)methylsulfinyl]-1H-benzimidazole, 1-(p-fluorobenzenesulfonyl)-5-methoxy-2-[(3,5-dimethyl-4-methoxy-2-pyridyl)methylsulfinyl]-1H-benzimidazole, 1-(p-fluorobenzenesulfonyl)-6-methoxy-2-[(3,5-dimethyl-4-methoxy-2-pyridyl)methylsulfinyl]-1H-benzimidazole, 1-(p-fluorobenzenesulfonyl)-5-difluoromethoxy-2-[(3,4-dimethoxy-2-pyridyl)methylsulfinyl]-1H-benzimidazole, 1-(p-fluorobenzenesulfonyl)-6-difluoromethoxy-2-[(3,4-dimethoxy-2-pyridyl)methylsulfinyl]-1H-benzimidazole, 1-(p-fluorobenzenesulfonyl)-2-[(3-methyl-4-(2',2',2'-trifluoroethoxy)-2-pyridyl)methylsulfinyl]-1H-benzimidazole, 1-(p-methylbenzenesulfonyl)-5-methoxy-2-[(3,5-dimethyl-4-methoxy-2-pyridyl)methylsulfinyl]-1H-benzimidazole, 1-(p-methylbenzenesulfonyl)-6-methoxy-2-[(3,5-dimethyl-4-methoxy-2-pyridyl)methylsulfinyl]-1H-benzimidazole, 1-(p-methylbenzenesulfonyl)-5-difluoromethoxy-2-[(3,4-dimethoxy-2-pyridyl)methylsulfinyl]-1H-benzimidazole, 1-(p-methylbenzenesulfonyl)-6-difluoromethoxy-2-[(3,4-dimethoxy-2-pyridyl)methylsulfinyl]-1H-benzimidazole, 1-(p-methylbenzenesulfonyl)-2-[(3-methyl-4-(2',2',2'-trifluoroethoxy)-2-pyridyl)methylsulfinyl]-1H-benzimidazole, 1-(p-methoxybenzenesulfonyl)-5-methoxy-2-[(3,5-dimethyl-4-methoxy-2-pyridyl)methylsulfinyl]-1H-benzimidazole, 1-(p-methoxybenzenesulfonyl)-6-methoxy-2-[(3,5-dimethyl-4-methoxy-2-pyridyl)methylsulfinyl]-1H-benzimidazole, 1-(p-methoxybenzenesulfonyl)-5-difluoromethoxy-2-[(3,4-dimethoxy-2-pyridyl)methylsulfinyl]-1H-benzimidazole, 1-(p-methoxybenzenesulfonyl)-6-difluoromethoxy-2-[(3,4-dimethoxy-2-pyridyl)methylsulfinyl]-1H-benzimidazole, 1-(p-methoxybenzenesulfonyl)-2-[(3-methyl-4-(2',2',2'-trifluoroethoxy)-2-pyridyl)methylsulfinyl]-1H-benzimidazole, 1-(3-trifluoromethylbenzenesulfonyl)-5-methoxy-2-[(3,5-dimethyl-4-methoxy-2-pyridyl)methylsulfinyl]-1H-benzimidazole, 1-(3-trifluoromethylbenzenesulfonyl)-6-methoxy-2-[(3,5-dimethyl-4-methoxy-2-pyridyl)methylsulfinyl]-1H-benzimidazole, 1-(3-trifluoromethylbenzenesulfonyl)-5-difluoromethoxy-2-[(3,4-dimethoxy-2-pyridyl)methylsulfinyl]-1H-benzimidazole, 1-(3-trifluoromethylbenzenesulfonyl)-6-difluoromethoxy-2-[(3,4-dimethoxy-2-pyridyl)methylsulfinyl]-1H-benzimidazole, 1-(3-trifluoromethylbenzenesulfonyl)-2-[(3-methyl-4-(2',2',2'-trifluoroethoxy)-2-pyridyl)methylsulfinyl]-1H-benzimidazole, 1-(p-trifluoromethoxybenzenesulfonyl)-5-methoxy-2-[(3,5-dimethyl4-methoxy-2-pyridyl)methylsulfinyl]-1H-benzimidazole, 1-(p-trifluoromethoxybenzenesulfonyl)-6-methoxy-2-[(3,5-dimethyl-4-methoxy-2-pyridyl)methylsulfinyl]-1H-benzimidazole, 1-(p-trifluoromethoxybenzenesulfonyl)-5-difluoromethoxy-2-[(3,4-dimethoxy-2-pyridyl)methylsulfinyl]-1H-benzimidazole, 1-(p-trifluoromethoxybenzenesulfonyl)-6-difluoromethoxy-2-[(3,4-dimethoxy-2-pyridyl)methylsulfinyl]-1H-benzimidazole, 1-(p-trifluoromethoxybenzenesulfonyl)-2-[(3-methyl-4-(2',2',2'-trifluoroethoxy)-2-pyridyl)methylsulfinyl]-1H-benzimidazole, 1-(p-dimethylaminobenzenesulfonyl)-5-methoxy-2-[(3,5-dimethyl-4-methoxy-2-pyridyl)methylsulfinyl]-1H-benzimidazole, 1-(p-dimethylaminobenzenesulfonyl)-5-difluoromethoxy-2-[(3,4-dimethoxy-2-pyridyl)methylsulfinyl]-1H-benzimidazole, 1-(p-dimethylaminobenzenesulfonyl)-2-[(3-methyl-4-(2',2',2'-trifluoroethoxy)-2-pyridyl)methylsulfinyl]-1H-benzimidazole, 1-(p-ethoxycarbonylbenzenesulfonyl)-5-methoxy-2-[(3,5-dimethyl-4-methoxy-2-pyridyl)methylsulfinyl]-1H-benzimidazole, 1-(p-ethoxycarbonylbenzenesulfonyl)-2-[(3-methyl-4-(2',2',2'-trifluoroethoxy)-2-pyridyl)methylsulfinyl]-1H-benzimidazole.

7. A pharmaceutical composition comprising a pharmaceutically acceptable excipient and a prodrug of a proton pump inhibitor in accordance with claim 1.

8. A pharmaceutical composition comprising a pharmaceutically acceptable excipient and a prodrug of a proton pump inhibitor in accordance with claim 3.

9. A pharmaceutical composition comprising a pharmaceutically acceptable excipient and a prodrug of a proton pump inhibitor in accordance with claim 2.

10. A pharmaceutical composition in accordance with claim 7, 8 or 9, said composition comprising a liquid adapted for injection to a mammal, said liquid having a pH not exceeding 8.5 pH units.

* * * * *

UNITED STATES PATENT AND TRADEMARK OFFICE
CERTIFICATE OF CORRECTION

PATENT NO. : 6,093,734
DATED : July 25, 2000
INVENTOR(S) : Garst et al.

It is certified that error appears in the above-identified patent and that said Letters Patent is hereby corrected as shown below:

Title page,
Item [56], under FOREIGN PATENT DOCUMENTS, "00452200" should be -- 0045200 --.

Column 5,
Line 29, "suffoxides" should be -- sulfoxides --.

Column 6,
Line 19, after "in", "a" should be -- α --.

Column 7,
Line 7, "usefull" should be -- useful --.

Column 9,
Line 26, after "3,5", insert -- - --.
Line 65, "(2' ,2 '-" should be -- (2',2',2'- --.

Column 13,
Line 1, "disulfide" should be -- sulfide --.
Line 4, "disulfide" should be -- sulfide --.
Line 5, "disulfides" should be -- sulfides --.
Reaction Scheme 2, the structure of Formula 18 should be -- 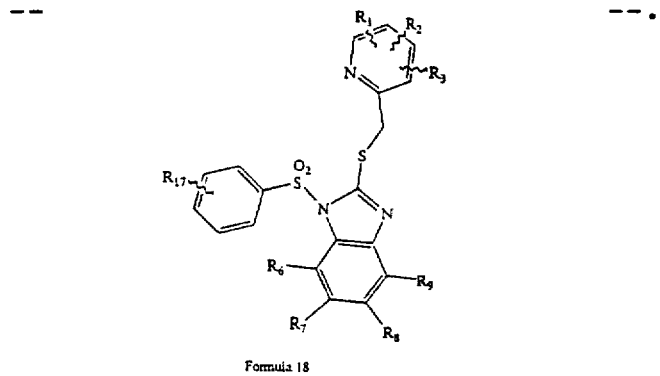 --.

Formula 18

UNITED STATES PATENT AND TRADEMARK OFFICE
CERTIFICATE OF CORRECTION

PATENT NO. : 6,093,734
DATED : July 25, 2000
INVENTOR(S) : Garst et al.

It is certified that error appears in the above-identified patent and that said Letters Patent is hereby corrected as shown below:

Column 16,
Line 62, delete "5".

Column 17,
Line 60, "3*0.5" should be -- 3±0.5 --.
Line 60, after ""°C", delete ".".

Column 18,
Line 5, after "C", delete ".".
Line 6, after ""°C", delete ".".
Line 16, after ""°C", delete ".".

Column 19,
Line 43, after "C", delete ".".
Line 53, "1H1" should be -- 1H --.

Column 20,
Line 13, after ""°C", delete ".".
Line 50, after ""°C", delete ".".

Column 21,
Line 49, after "$R_{10}$", delete ",".

Column 22,
Line 49, "2" should be -- 1 --.

Column 23,
Line 16, "b 1-" should be -- 1- --.
Line 49, "1-(p-methylbenzenesulfonyl)..." should start a new line.

UNITED STATES PATENT AND TRADEMARK OFFICE
CERTIFICATE OF CORRECTION

PATENT NO. : 6,093,734
DATED : July 25, 2000
INVENTOR(S) : Garst et al.

It is certified that error appears in the above-identified patent and that said Letters Patent is hereby corrected as shown below:

Column 24,
Line 24, after "dimethyl", insert -- - --.

Signed and Sealed this

Twenty-fifth Day of December, 2001

Attest:

Attesting Officer

JAMES E. ROGAN
Director of the United States Patent and Trademark Office